United States Patent
Sauter et al.

(10) Patent No.: US 7,909,802 B2
(45) Date of Patent: Mar. 22, 2011

(54) DEVICE FOR INSERTING A DRAIN AND HANDLE FOR SUCH A DEVICE

(75) Inventors: Bruno Sauter, Groningen (NL); Jacob Wilkens, Groningen (NL); Libbe Jitze Jonkman, Drachten (NL)

(73) Assignee: IMP B.V., Loenen A/D Vecht (NL)

( * ) Notice: Subject to any disclaimer, the term of this patent is extended or adjusted under 35 U.S.C. 154(b) by 657 days.

(21) Appl. No.: 10/554,349

(22) PCT Filed: Apr. 24, 2003
(Under 37 CFR 1.47)

(86) PCT No.: PCT/NL03/00304
§ 371 (c)(1),
(2), (4) Date: Mar. 5, 2007

(87) PCT Pub. No.: WO2004/093964
PCT Pub. Date: Nov. 4, 2004

(65) Prior Publication Data
US 2007/0250043 A1    Oct. 25, 2007

(51) Int. Cl.
*A61M 5/32* (2006.01)
*A61M 27/00* (2006.01)
(52) U.S. Cl. ........................ 604/272; 604/541
(58) Field of Classification Search .......... 604/272
See application file for complete search history.

(56) References Cited

U.S. PATENT DOCUMENTS

| | | | |
|---|---|---|---|
| 1,683,349 A | 9/1928 | Hein | |
| 3,104,448 A * | 9/1963 | Morrow et al. | 27/24.1 |
| 3,605,747 A | 9/1971 | Pashkow | |
| 3,774,606 A | 11/1973 | Norton | |
| 3,993,079 A | 11/1976 | Henriques de Gatztanondo | |
| 4,052,989 A | 10/1977 | Kline | |
| 4,308,875 A | 1/1982 | Young | |
| 4,617,929 A * | 10/1986 | Gill | 606/108 |
| 4,645,491 A | 2/1987 | Evans | |
| 4,721,506 A | 1/1988 | Teves | |
| 4,792,328 A | 12/1988 | Beck et al. | |
| 4,953,594 A | 9/1990 | Von Berg | |
| 4,973,313 A | 11/1990 | Katsaros et al. | |
| 5,137,517 A | 8/1992 | Loney et al. | |
| 5,149,324 A | 9/1992 | Clawson | |

(Continued)

FOREIGN PATENT DOCUMENTS

DE    44 16 976 A    11/1995

(Continued)

*Primary Examiner* — Nicholas D Lucchesi
*Assistant Examiner* — Jason Flick
(74) *Attorney, Agent, or Firm* — Pearne & Gorodn LLP

(57) ABSTRACT

A device for inserting a drain (5) into a wound includes a needle (1) and a handle (2) for holding the needle. The needle (1) has a sharp front end (3) and a rear end including a connector (4) for connection to a drain (5) for leading the drain (5) through a perforation in skin tissue made with the needle (1). The handle (2) projects in a longitudinal direction and detachably mountable to a portion (8) of the needle (1) extending in an axial direction. If the handle (2) is in mounted condition, the longitudinal direction in which the handle (2) projects is oriented at an angle (α) to the axial direction of the portion (8) of the needle (1) to which the handle (2) is mounted, so that operation of the needle (1) is facilitated.

13 Claims, 3 Drawing Sheets

U.S. PATENT DOCUMENTS

| | | | |
|---|---|---|---|
| 5,279,570 A | 1/1994 | Dombrowski et al. | |
| 5,334,150 A | 8/1994 | Kaali | |
| 5,376,076 A | 12/1994 | Kaali | |
| 5,380,291 A * | 1/1995 | Kaali | 604/164.08 |
| 5,520,654 A | 5/1996 | Wahlberg | |
| 5,531,701 A | 7/1996 | Luther | |
| 5,551,947 A | 9/1996 | Kaali | |
| 5,607,405 A * | 3/1997 | Decker et al. | 604/264 |
| 5,672,158 A | 9/1997 | Okada et al. | |
| 5,720,761 A | 2/1998 | Kaali | |
| 5,725,504 A | 3/1998 | Collins | |
| 5,846,221 A | 12/1998 | Snoke et al. | |
| 5,860,953 A | 1/1999 | Snoke et al. | |
| 5,893,837 A | 4/1999 | Eagles et al. | |
| 5,919,172 A | 7/1999 | Golba, Jr. | |
| 6,007,531 A | 12/1999 | Snoke et al. | |
| 6,017,322 A * | 1/2000 | Snoke et al. | 604/95.01 |
| 6,524,238 B2 | 2/2003 | Velikaris et al. | |
| 2002/0077530 A1 * | 6/2002 | Velikaris et al. | 600/213 |
| 2003/0195392 A1 | 10/2003 | Hamel et al. | |

FOREIGN PATENT DOCUMENTS

| | | |
|---|---|---|
| EP | 0623355 | 11/1994 |
| EP | 0 807 447 A1 | 11/1997 |
| JP | 47001145 U | 8/1972 |
| JP | 06063046 U | 9/1994 |
| JP | 10151204 A | 6/1998 |
| NL | 72 16 160 | 6/1973 |
| NL | 100 46 22 C | 5/1998 |
| RU | 2 155 077 C | 8/2000 |
| RU | 2155077 C1 * | 8/2000 |
| WO | 98/23321 | 6/1998 |
| WO | 0249521 A1 | 6/2002 |

* cited by examiner

DEVICE FOR INSERTING A DRAIN AND HANDLE FOR SUCH A DEVICE

TECHNICAL FIELD AND BACKGROUND ART

The invention relates to a device for inserting a drain into a wound according to the introductory portion of claim 1. The invention also relates to a handle for a device for inserting a drain into a wound according to the introductory portion of claim 12.

Such a device and such a handle are known from international patent application WO 98/23321. Such a device and such a handle are also known from German patent application 44 16 976.

In the treatment of open wounds, in particular deep wounds caused by surgical treatment, drains are placed before the wound is closed.

For placement of the drains, the sharp frontal end of the needle, is penetrated through the patient's skin from the inside to the outside near the wound and the needle and the drain attached thereto are drawn through the skin from the inside to the outside of the skin leaving the, usually perforated, upstream end portion of the drain in the wound. Next, the drain is detached from the needle and attached in a manner known in itself to an apparatus (such as a Redon bottle) for draining off wound fluid and the like. The entry end of the drain may also be arranged in foam material in the wound to obtain drainage from the wound over a large surface. After the positioning of the drain or drains, the wound is closed and may be sealed.

The needle has a shaft with a sharp front end and a rear end adapted for connection to the drain such that the drain is reliably secured to the needle. The external cross-sectional size of the drain is not substantially larger than the external cross-sectional size of the needle for easy passage of the transition from the shaft to the drain through the skin.

Piercing the skin with the needle requires much force because of the toughness of the skin. As the needle has to have a minimal diameter, in the order of the diameter of the drain to be applied, the surface of the needle forms only a small contact area and the performing person (for instance, a surgeon) generally wears surgical gloves, which have typically become slippery from wound fluid, blood and the like, affording little grip. Therefore, when using devices for inserting a drain as described in for instance European patent application 0 623 355 and Dutch patent application 72 16 160, it is difficult to exert the required force. Moreover, the shaft of the needle is slightly curved to facilitate leading the tip of the needle under the skin to the position where the skin is to be perforated. The small and essentially circular cross-section of the needle provides little grip to control its rotational orientation about the longitudinal axis of the needle, so that the tip of the needle can easily twist away from its orientation curved towards the inside of the skin to be perforated.

To facilitate the exertion of the required force for piercing the skin and providing better control to avoid undesired rotation of the needle about the longitudinal axis of the shaft, the known devices of the initially identified type each include a handle. The handle is detachably connected to the rear end of the needle, to which also the drain is connected, and has a central channel for at least partially receiving the drain.

The needle is pierced through the skin with the handle providing a large grip surface. After the needle has penetrated the skin sufficiently far, the needle is detached from the handle and the needle is drawn through the skin until the frontal end of the drain protrudes through the skin. The handle may for instance be withdrawn from the needle and the drain in the opposite direction and then be removed from the wound. Finally, the needle and the drain may be disconnected, and the drain may be prepared for use in the conventional manner.

Since the rear end of the needle is now provided with a handle, the needle itself may be less long than needles that are used without a handle and still be sufficiently long to allow the tip of the needle to be guided under the skin from the wound to the desired perforation position. As needles for leading a drain through the skin are generally used only once, a shorter needle produces less waste, resulting in a reduction in costs. The handle may also be disposable or be reused.

In spite of the curvature of the needle, accurately guiding the tip of the needle to the perforation position and perforating the skin still requires ergonomically awkward movements of the hand of the operator of the device, which interferes with accurate control during positioning of the tip of the needle and piercing of the skin.

SUMMARY OF THE INVENTION

It is an object of the invention to provide a device for inserting a drain into a wound of which can be operated operation more easily.

According to the present invention, this object is achieved by providing a device according to claim 1. The invention can also be embodied in a handle according to claim 12, which can be combined with a needle, to obtain a device according to claim 1.

The angle between the longitudinal direction in which the handle projects and the axial direction of the portion of the needle to which the handle is mounted, allows the operator of the device to hold the device gripped with the full hand in an orientation in which the needle extends medially and proximally while the handle is held in a hand that is held in a neutral position, so that the tip of the needle can easily and accurately be guided to the perforation position and the forces required for perforating the skin can be exerted relatively easily.

Particular embodiments of the invention are set forth in the dependent claims.

DETAILED DESCRIPTION

Figure 1:
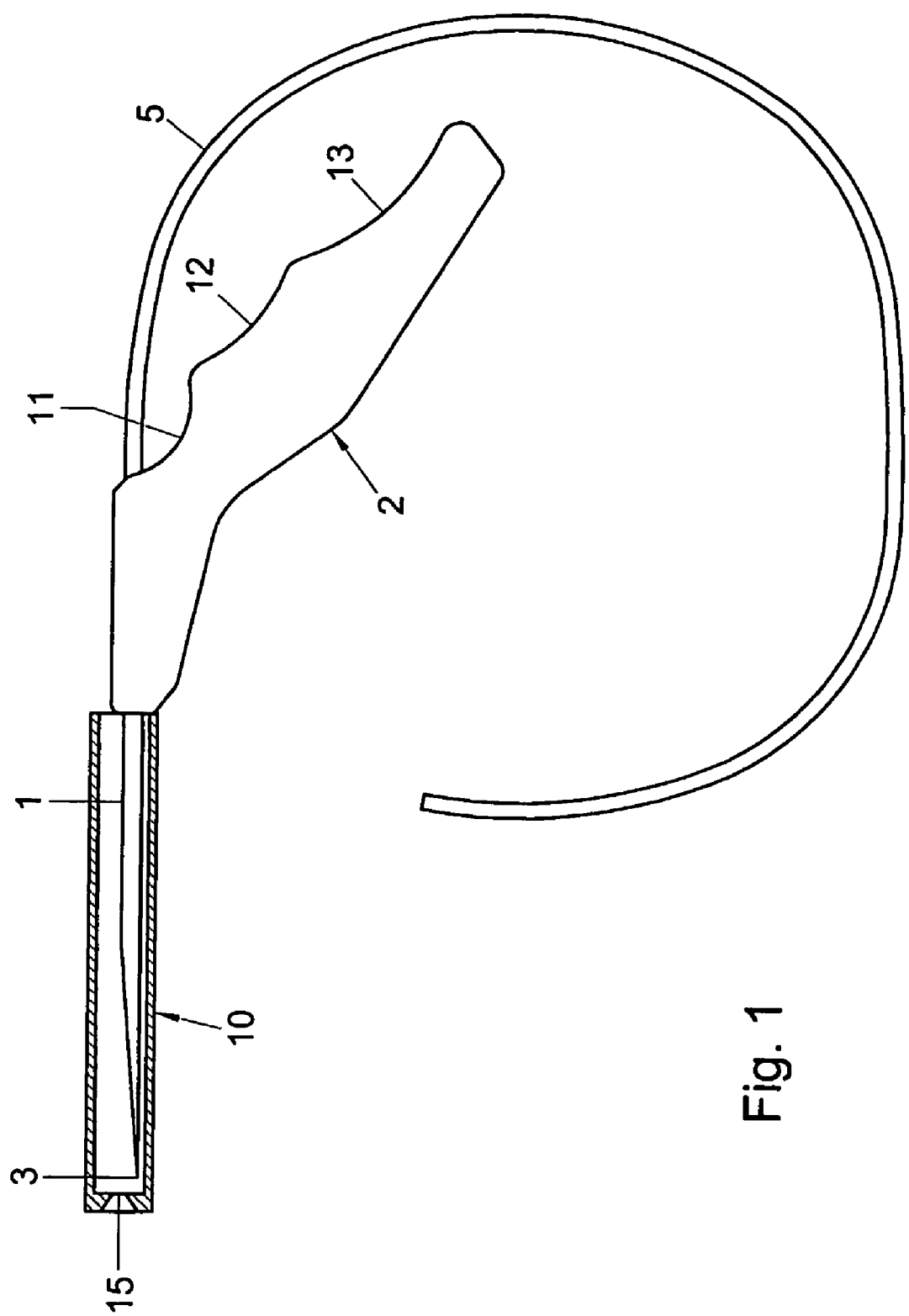
FIG. 1 is a side view of an example of device according to the invention in a condition for packaging and before use, a pull through member of the device being shown in cross-section along its centerline.

The device according to presently most preferred embodiment of the invention shown in the drawings includes a needle 1 and a handle 2. At its front end, the needle 1 has a sharp point 3 and at its rear end the needle 1 has a connector 4. The connector is adapted for connecting a drain 5 to the connector 4 in an in-line configuration with the needle 1. According to this example, the connector 4 is a stub provided with a fine thread, over which the end of the drain 5 is clasped. Depending on the size and location of the wound, the drain preferably has a size selected from a range of French gauge 6-18 (2-6 mm diameter). Furthermore, the cross-sectional size of the needle 1 is preferably not substantially smaller than the cross-sectional size of the drain 5, even where it is mounted to the connector, to avoid when threading the drain through the perforation. More preferably, the cross-sectional size of the needle 1 is slightly large than the cross-sectional size of the drain 5.

Figure 2:
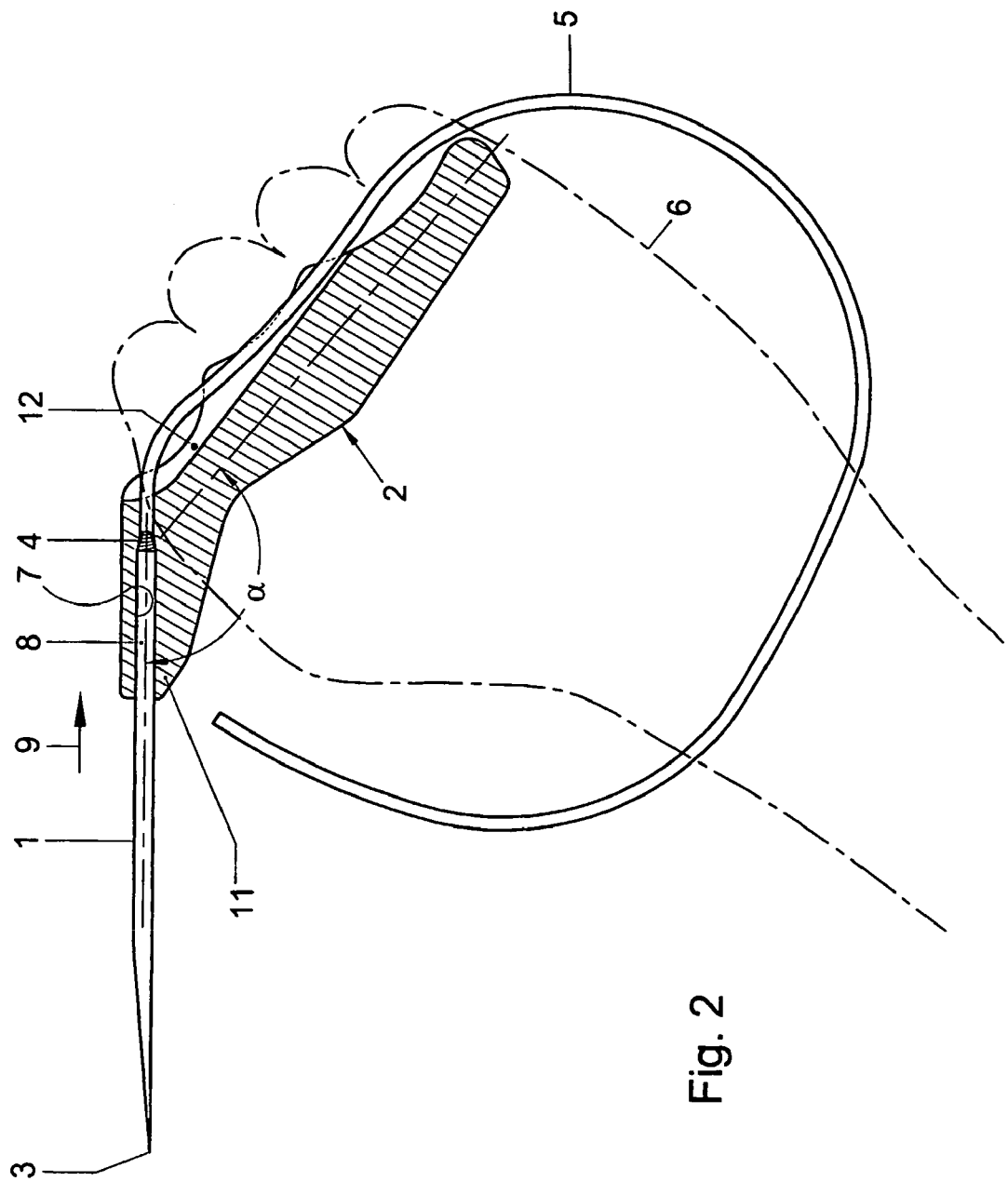
FIG. 2 is a side view in cross section of the device according to FIG. 2 without the pull through member, in operating condition.

The handle 2 has an elongate shape allowing it to be gripped fully by a human hand 6 as schematically indicated in FIG. 2. According to the present example, the handle 2 is of plastic material. A recess in the form of a channel 7 extends through the handle 2. At one end, the channel 7 has an interior shape that corresponds to the exterior shape of a rear portion 8 of the needle 1. By threading the drain 5 and subsequently the needle 1 into the channel 7 in a rearward direction as indicated by an arrow 9 in FIG. 2, the handle 2 is detachably mounted to a rear end portion of the needle 1. Mounting the handle 2 to the needle 1 may for instance be performed by the operating surgeon or by an assistant. However, the assembly of the device is preferably conducted industrially under sterile conditions after which the device is packaged in the pre-assembled condition shown in FIG. 1 in which a pull through member 10 forms a sheath protecting, on the one hand, the needle 1 and, on the other hand, the packaging and the user from the needle 1 sharp needle tip 3.

The inside diameter of the channel 7 is slightly smaller toward the rear end of the channel 7, so that the needle 1 is prevented from being pushed backward further. Thus, the needle 1 is not only fixed laterally relative to the handle by a close and preferably slightly tight fit in the channel 7, but also axially by the slight restriction in the channel 7 near its rear end, so that the needle 1 and the handle 2 are mountable to each other in a fixed position.

In mounted condition, the longitudinal direction of the handle 2 is is oriented at an angle $\alpha$ to the axial direction of the portion of the needle 1 to which the handle 2 is mounted. In the handle 2 according to the present example, this is effect is obtained because the longitudinal direction of the elongate handle 2 is oriented at an angle to the axial direction of the channel-shaped recess 7 for detachably receiving the portion of the needle 1 to which the handle 2 is mounted.

The angle $\alpha$ between the longitudinal direction of the elongate handle 2 (or at least the portion of the handle 2 adapted to be held by the hand 6, i.e. disregarding the projection 11 of the handle 2 parallel to the needle 1) and the axial direction of the portion of the needle 1 to which the handle 2 is mounted, allows the operator of the device to hold the device gripped with the full hand 6 in an orientation in which the needle 1 extends medially and proximally while the hand 6 holding the handle 2 is held in a neutral position. Therefore, the tip 3 of the needle 1 can easily and accurately be guided under the skin to the perforation position and the forces required for perforating the skin can be exerted relatively easily.

As can further be seen, the side of the handle 2 facing away from the front needle tip 3 is provided with bays 11-13 for receiving portions of the fingers of the person operating the device, so that additional grip to the handle 2 is provided.

Because the portion of the needle 1 to which the handle 2 is mountable is a rear end portion of the needle 1, the needle 1 can be relatively short.

An additional advantage of the angle $\alpha$ between the handle 2 and the needle 1 is, that the curvature conventionally provided in the needle to point the tip towards the inside of the skin to be perforated is not required or can at least be substantially reduced. Firstly, when pushing the needle to the perforation position and when the needle is subsequently threaded through the tissue to pull trough the drain, the curvature of the needle can cause additional traumatizing tissue displacement. Secondly, bending the needle to obtain the required curvature adds to the costs of the needle, which is particularly undesirable because the needle is typically used only once and then disposed of. Accordingly, by providing the device with a needle 1 that is straight, the orientation of the needle tip 3 caused by the angle between the handle 2 and the portion of the needle 1 to which the handle 2 is mounted is optimally used to avoid the disadvantages associated with curved needles. Nevertheless, a curved needle 1 can be provided within the framework of the invention, for instance to meet requirements resulting from particular wound locations and shapes or particular surgical techniques.

Because the needle 1 is not curved, there is no arm of significant length for exerting a torque about the axis of the portion of the needle 1 to which the handle 2 is mounted and causing undesired rotation of the needle 1 relative to the handle 2 about the axis of the portion of the needle 1 to which the handle 2 is mounted. Moreover, even if the needle 1 is rotated about the axis of the portion of the needle 1 to which the handle is mounted, this is of little importance, because such axial rotation of the needle 1 is of no significant influence on the direction in which the tip 3 of the straight needle 1 points.

In turn, the absence of significant torque exerted about the axis of the portion of the needle 1 to which the handle 2 is mounted and the absence of significant disadvantageous effects of any axial rotation of the straight needle 1, allows leaving out measures to prevent the needle 1 from rotating axially. According to the present example these effects are used for keeping manufacturing costs low by providing that the portion of the needle 1 to which the handle 2 is mountable or mounted has a circular outer circumference. Furthermore, also the channel 7 can simply be provided as a circular bore which further contributes to bringing manufacturing costs down.

The angle $\alpha$ between the handle 22 and the portion of the needle 1 to which the handle is mounted is preferably at least 20° and more preferably at least 30°, so that a substantive effect on the orientation of the tip 3 of the needle 1 is obtained. Furthermore, the angle $\alpha$ is preferably at most 70° and more preferably at most 55°. to allow to guide the needle tip 3 accurately to the perforation position.

To reduce contact between the drain 5 and tissue in the wound during the insertion of the needle 1 and the perforation of the skin, the handle 2 has a gutter 12 facing away from the front end 3 of the needle 1 if the device is in mounted condition. The gutter 12 has a width and depth adapted for accommodating at least a portion of a drain 5 connected to the rear end of the needle 1 if the device is in mounted condition. As is best seen in FIG. 2, the person operating the device can simply hold the portion of the drain 5 adjacent the handle 2 in the gutter 12, by holding the handle 2 and the portion of the drain 5 next to the handle 2 together in the hand 6.

Figure 3:
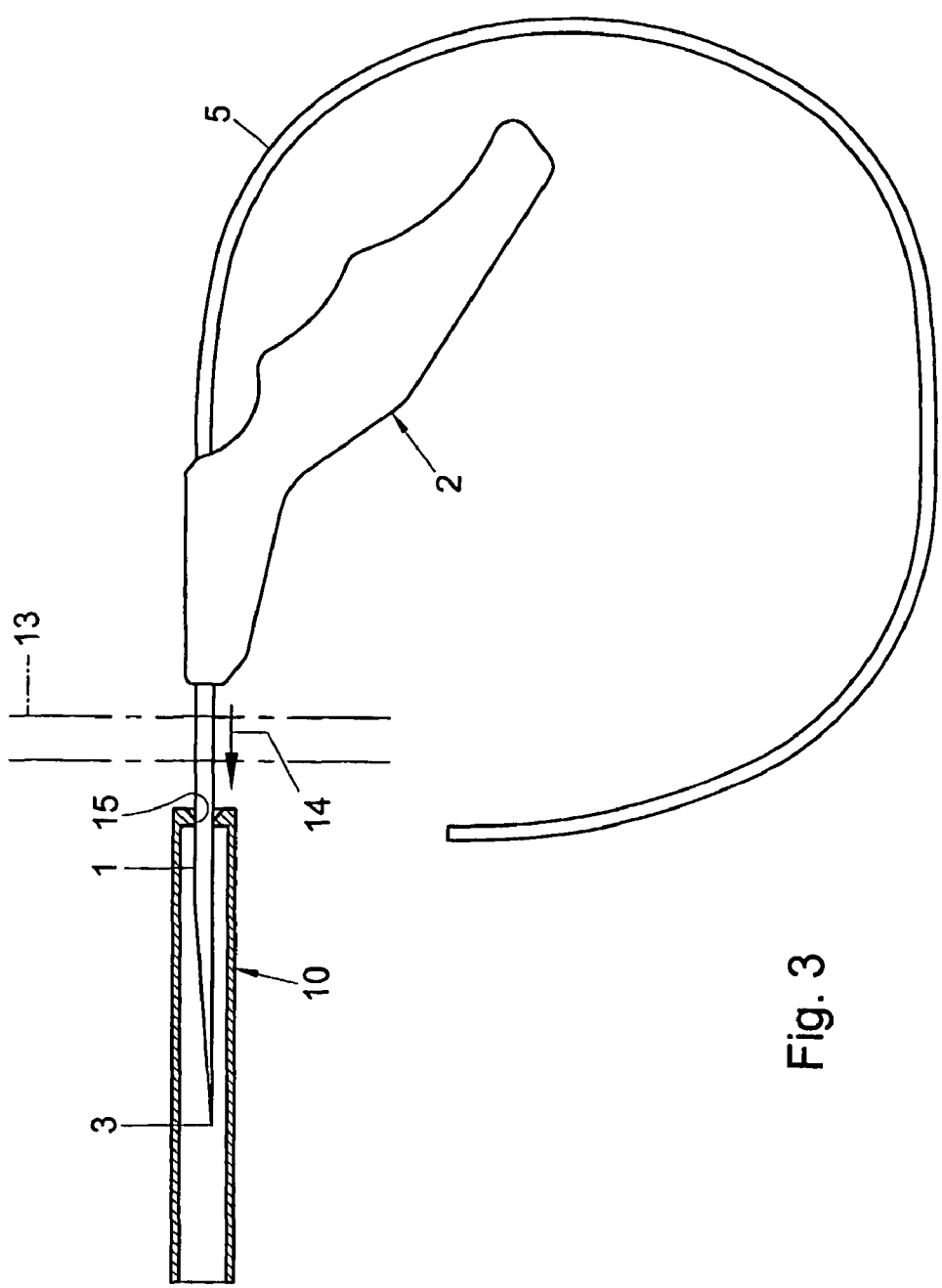
FIG. 3 is a side view of the device according to FIGS. 2 and 3 in a subsequent operating condition, the pull through member of the device being shown in cross-section along its centerline.

In FIG. 3, the skin 13 perforated by the needle is schematically shown. For placing the drain, the front end of the needle 1 needs to be pulled outwardly though the skin 13 from the outside of the skin, until the right length of drain tube 5 is left inside the patient. Conventionally, this is carried out by grabbing the needle by hand and then manually pulling the needle out of the skin. However, the sharp tip 3 of the needle 1 emerging from the skin surface causes a substantial risk of injury for the hand held in the vicinity of the needle tip 3 for grabbing the needle 1. Such injury is not only harmful, but also entails a risk of infection.

To reduce the risk of injury when engaging the needle 1 emerging outwardly from the skin 13, the device according to the present example further includes a pull through member 10 for receiving at least a front end portion of the needle 1 and engaging a portion of the needle in front of the handle 2 mounted to the needle 1. Since the needle 1 is not engaged directly, the risk of injury is substantially reduced. The pull through member 10 may also be used for exerting a counterforce to the outside of the skin 13 to facilitate perforation.

Because the pull through member 10 is separate from the handle 2, the pull through member 10 can also be used to pull the needle 1 forwardly out of the handle 2 in the direction indicated by arrow 14 in FIG. 3. To finally also remove the drain 5 from the channel 7 in the handle 7, the handle 2 is slid along the drain 5 towards its tail end remote from the needle 1.

As was initially described, according to the present example, the pull through member is provided in the form of a sheath for receiving at least a front portion of the needle 1 projecting from the handle 2, so that the pull through member 10 also functions as a packaging element shielding off the sharp tip 3 of the needle 1. For the packaging function, the needle is inserted in the pull through member 10 at the end having the widest opening.

For engaging the needle 1, the pull through member 10 includes a needle engagement passage 15 at its opposite end for engaging a portion of the needle 1 extending through that passage 15.

At least before the needle 1 has been inserted into needle engagement passage 15, this passage 15 has a cross-section smaller than the cross-section of the needle portion engageable thereby. Thus, the engagement of the needle 1 is achieved by clamping of the passage 15 around the needle 1 as the needle penetrating into the passage 15 widens it. This allows to achieve the required engagement of the needle without engaging projections or recesses in the circumferential surface of the needle 1. Such projections or recesses would hinder a smooth passage of the needle through the perforation formed in the skin 13 an entail a risk of additional traumatization of skin tissue.

According to the present example, a particularly effective engagement is achieved, because the needle engagement passage 15 has a cross-section decreasing in the direction in which the needle 1 is inserted into the passage 15. Due to this configuration, pulling forces tending to retract the needle 1 from the pull through member 10 cause normal forces exerted by the passage 15 onto the needle 1 to increase, so that the engagement of the needle 1 becomes firmer. Accordingly, a very reliable engagement of the needle 1 is achievable even if the needle 1 is inserted into the pull through member with relatively little effort.

The invention is not limited to the embodiment described above. Within the scope of the invention as specified by the claims, many other embodiments are conceivable. For instance the handle may engage the needle in another manner and/or in another position, a pull through member may be absent or provided in another form engaging the needle with different clamping means such as wedge elements, the needle may have a different overall shape, cross-section and/or tip etc.

The invention claimed is:

1. A device for inserting a drain into a wound, the device comprising a needle, a drain and a handle, the needle having a sharp front end effective for perforating a skin, the drain being connected to a rear end of the needle, the handle having a gripping portion and a needle-holding portion the needle-holding portion having a channel, a rear portion of the needle extending in an axial direction and being mounted in the channel, the needle being removable from the channel only in a forward direction, said forward direction being parallel to said axial direction and pointing from the needle's rear end towards the needle's front end, wherein said needle is configured so that said needle can completely exit said needle-holding portion in said forward direction, the handle gripping portion being elongated in a longitudinal direction and configured so that a person can grip the gripping portion with a single hand and, with only said single hand, effectively manipulate the device in connection with perforating the skin with the needle, a line defined by the longitudinal direction of the handle gripping portion and a line defined by the axial direction of the rear portion of the needle forming an acute angle, the device being configured so that the drain passes through the channel when the needle is removed from the channel in the forward direction.

2. A device according to claim 1, wherein the needle is straight.

3. A device according to claim 2, wherein the rear portion of the needle has a circular outer circumference.

4. A device according to claim 1, wherein said angle is at least 20° and at most 70°.

5. A device according to claim 1, wherein the handle has a gutter facing away from the front end of the needle, the gutter having a width and depth adapted for accommodating at least a portion of the drain.

6. A device according to claim 1, further including a pull through member for receiving at least a front end portion of the needle and engaging a portion of the needle in front of the handle mounted to the needle.

7. A device according to claim 6, wherein the pull through member includes a needle engagement passage for engaging a portion of the needle extending through said passage.

8. A device according to claim 7, wherein, at least before said needle has been inserted into said needle engagement passage, said passage has a cross-section smaller than the cross-section of the needle portion engageable by said passage.

9. A device according to claim 6, wherein said pull through member forms a sheath for receiving at least a front portion of the needle projecting from the handle.

10. The device according to claim 1, wherein said angle is at least 30°.

11. The device according to claim 1, wherein said angle is at most 55°.

12. The device according to claim 1, wherein said angle is at least 30° and at most 55°.

13. The device according to claim 1, wherein the needle can be disengaged from the needle-holding portion by a method consisting of gripping the needle and pulling the needle straight out of the channel.

* * * * *

UNITED STATES PATENT AND TRADEMARK OFFICE
CERTIFICATE OF CORRECTION

| | | |
|---|---|---|
| PATENT NO. | : 7,909,802 B2 | Page 1 of 1 |
| APPLICATION NO. | : 10/554349 | |
| DATED | : March 22, 2011 | |
| INVENTOR(S) | : Sauter et al. | |

It is certified that error appears in the above-identified patent and that said Letters Patent is hereby corrected as shown below:

In column 6, line 6, in Claim 1, please delete "a gripping portion and a needle-holding portion the needle-holding portion" and insert therefor -- a gripping portion and a needle-holding portion, the needle-holding portion--.

Signed and Sealed this
Twenty-first Day of June, 2011

David J. Kappos
*Director of the United States Patent and Trademark Office*